(12) United States Patent
Fenske

(10) Patent No.: US 8,047,893 B2
(45) Date of Patent: Nov. 1, 2011

(54) POSTURE SUPPORT GARMENT

(76) Inventor: Mary C. Fenske, Kirkland, WA (US)

( * ) Notice: Subject to any disclaimer, the term of this patent is extended or adjusted under 35 U.S.C. 154(b) by 394 days.

(21) Appl. No.: 12/273,170

(22) Filed: Nov. 18, 2008

(65) Prior Publication Data

US 2009/0126084 A1 May 21, 2009

Related U.S. Application Data

(60) Provisional application No. 61/003,739, filed on Nov. 19, 2007.

(51) Int. Cl.
 *A41C 3/00* (2006.01)
(52) U.S. Cl. ............................................. 450/86; 450/85
(58) Field of Classification Search .................. 450/59, 450/62, 64, 85, 86, 1, 2, 7, 8; 2/44, 45, 92, 2/326, 327; 128/99.1, 100.1, 101.1
See application file for complete search history.

(56) References Cited

U.S. PATENT DOCUMENTS

| | | | |
|---|---|---|---|
| 224,784 A | 2/1880 | Johnstone | |
| 245,655 A | 8/1881 | Phelp | |
| 317,474 A | 5/1885 | Strouse | |
| 770,752 A * | 9/1904 | Hull | 2/54 |
| 1,129,515 A | 2/1915 | Perry | |
| 2,477,792 A * | 8/1949 | Fratianni | 450/2 |
| 2,591,462 A * | 4/1952 | Mungo | 450/2 |
| 2,672,613 A * | 3/1954 | Popp | 450/86 |
| 2,752,601 A * | 7/1956 | Gluckin | 450/86 |
| 2,782,416 A * | 2/1957 | Ginsburg | 450/70 |
| 3,008,468 A * | 11/1961 | Williams | 450/2 |
| 3,027,898 A | 3/1962 | Williams | |
| 3,856,004 A | 12/1974 | Cox | |
| 4,459,979 A | 7/1984 | Lewis, Jr. | |
| 5,256,135 A | 10/1993 | Avihod | |
| 5,823,851 A | 10/1998 | Dicker | |
| 5,950,628 A | 9/1999 | Dunfee | |
| 6,280,287 B1 * | 8/2001 | Keith et al. | 450/1 |
| 6,302,761 B1 | 10/2001 | Wrenn | |
| 6,315,747 B1 | 11/2001 | Toole | |
| 6,336,458 B1 | 1/2002 | Nafziger | |
| 6,386,944 B2 * | 5/2002 | Keith et al. | 450/1 |
| 6,440,094 B1 | 8/2002 | Maas | |
| 6,540,707 B1 | 4/2003 | Stark et al. | |
| 6,676,617 B1 | 1/2004 | Miller | |
| 6,709,411 B1 | 3/2004 | Olinger | |
| 6,936,021 B1 | 8/2005 | Smith | |
| 7,374,523 B2 | 5/2008 | Weir et al. | |
| 2002/0052568 A1 | 5/2002 | Houser et al. | |
| 2005/0197607 A1 | 9/2005 | Brown | |
| 2006/0064045 A1 | 3/2006 | Khavari | |

\* cited by examiner

*Primary Examiner* — Gloria Hale
(74) *Attorney, Agent, or Firm* — Polly L. Oliver

(57) ABSTRACT

A posture support garment comprises shoulder cap straps designed to pull the shoulders back thereby straightening the wearer's posture. The shoulder cap straps may be lined with silicone or some other appropriate material to grip or "grab" the skin at the area of the pectoral muscles or may be designed to cup the shoulders mechanically. This invention provides an effective posture enhancement while also providing a garment that is comfortable to wear all day. The posture support garment may be integrally designed and manufactured into a brassiere, T-shirt, bodice, or other top garment. The posture support garment may be worn by computer users or others concerned with detrimental genetic posture or the detrimental effects of everyday activity.

17 Claims, 9 Drawing Sheets

POSTURE SUPPORT GARMENT

RELATED APPLICATIONS

This application is related to and claims priority under 35 U.S.C. 119(e) to U.S. provisional application Ser. No. 61/003,739, entitled "Wearable Support Brace," filed on Nov. 19, 2007, with inventor Mary Fenske, which is hereby incorporated by reference in its entirety.

FIELD OF THE INVENTION

This invention pertains generally to garments and braces and more particularly to a garment or brace for the upper torso that offers posture support.

BACKGROUND OF THE FIELD

Many people experience pain in the shoulders, arms, back and/or neck due to poor posture—often from being hunched over working at computers (or indeed from genetic history). In addition to the pain—which can spread e.g., to elbows, wrists, and hands if not treated, people can suffer limited and stiff arm movement and deteriorating posture. Sufferers who may be at added risk are those with osteoporosis and women due to the weight of their breasts. These sufferers sometimes frequent chiropractors, massage therapists, physical therapists, and other practitioners to alleviate their pain and improve their movement. Sufferers also often resort to pain medication and muscle relaxers.

One method of attempting to relieve these sufferers is by "taping"—applying adhesive tape to the affected areas. However, such taping irritates skin and is designed only to help the patient "remember" to stand/sit up straight. There remains a need for a support brace that will offer real relief and will also be comfortable to wear for extended periods of time. There remains a need for a brace that will support the straightening of the spine as well as the pulling the shoulders back. Further, this support brace should be adjustable to fit wearers of various shapes and sizes but also so that the wearer can loosen or tighten the brace while wearing it throughout the day.

SUMMARY OF THE INVENTION

The present invention solves the above-mentioned problems by providing a solution having combined a support brace with a wearable garment for the upper torso that is both effective and comfortable for daily wear. The support garment may comprise a body harness to be incorporated into a brassiere, T-shirt, bodice, or other upper torso garment. The harness may comprise a plurality of straps, including at least two shoulder cap straps that are constructed to pull the shoulders backward, thereby straightening the wearer's posture. The cap straps may be lined with silicone (typically a latex-free silicone) or some other appropriate material to grip or "grab" the skin (from the pectoral muscle area and across the top of the respective shoulders) or they may use a physical design which mechanically grips or grabs the fronts of the shoulders and pulls them back.

One embodiment of the invention comprises a four-strap design in a brassiere-type undergarment. This embodiment includes the typical body band, breast cups, and shoulder straps of a conventional brassiere, but also includes two outer shoulder cap straps lined with silicone. This four-strap design may be incorporated into e.g., a sport bra or fashion bra, and the various straps may be made adjustable using mechanical means such as conventional buckles or hook-and-loop fasteners. To reduce or eliminate the need for the wearer to disrobe in order to make adjustments, the adjustability may alternatively be accomplished using electronic or other mechanical means (such as pull cords). A male version of this type embodiment may comprise similar bands and straps without the breast cups.

Alternate embodiments may comprise the various elements of the invention being integral to a T-shirt, blouse, bodice, or other top outer garment. In these embodiments, the body band and the straps may be integral with the appropriately-chosen garment material. The outer shoulder cap straps may be areas of silicone adhered to the inside of the garment in locations to be adjacent to the particular body areas of pectoral muscles and shoulders.

BRIEF DESCRIPTION OF THE DRAWINGS

The objects, features, and advantages of the present invention will be apparent to one skilled in the art from reading the following description in which.

DETAILED DESCRIPTION

The following specification describes a posture support garment apparatus and method. In the description, specific materials and configurations are set forth in order to provide a more complete understanding of the present invention. But it is understood by those skilled in the art that the present invention can be practiced without those specific details. In some instances, well-known elements are not described precisely so as not to obscure the invention.

Figure 1:
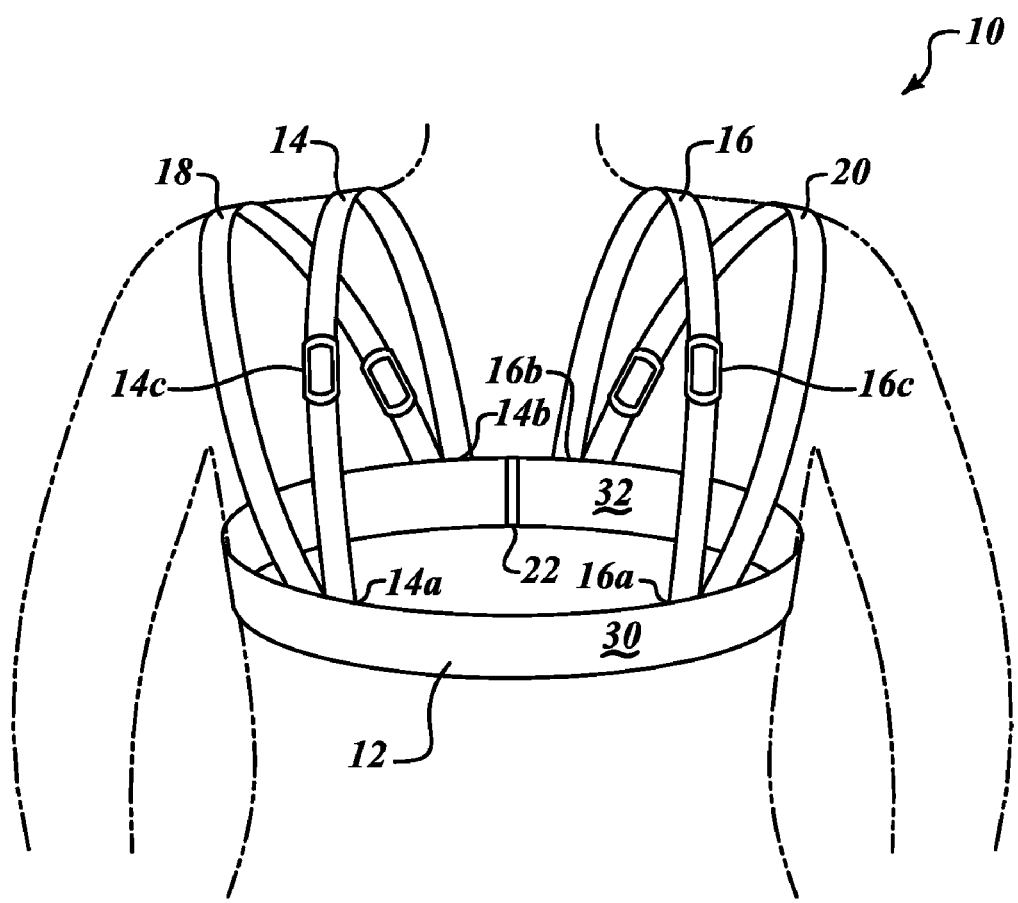
FIG. 1 is a perspective view of the basic concept model with conventional buckles.

FIG. 1 shows how the basic concept embodiment of the invention of the posture support garment 10 comprises a body band 12 and two sets of straps—the inner shoulder straps 14 and 16 and the outer shoulder cap straps 18 and 20. The body band is considered to have a front portion 30 corresponding to the front of the wearer's torso and a back portion 32 corresponding to the back side of the wearer's torso. The body band 12 also will typically have a closure 22 that may be in the back portion (front portion, or on the side) and that may comprise appropriate fasteners such as hook-and-eye or hook-and-loop fasteners.

Figure 2:
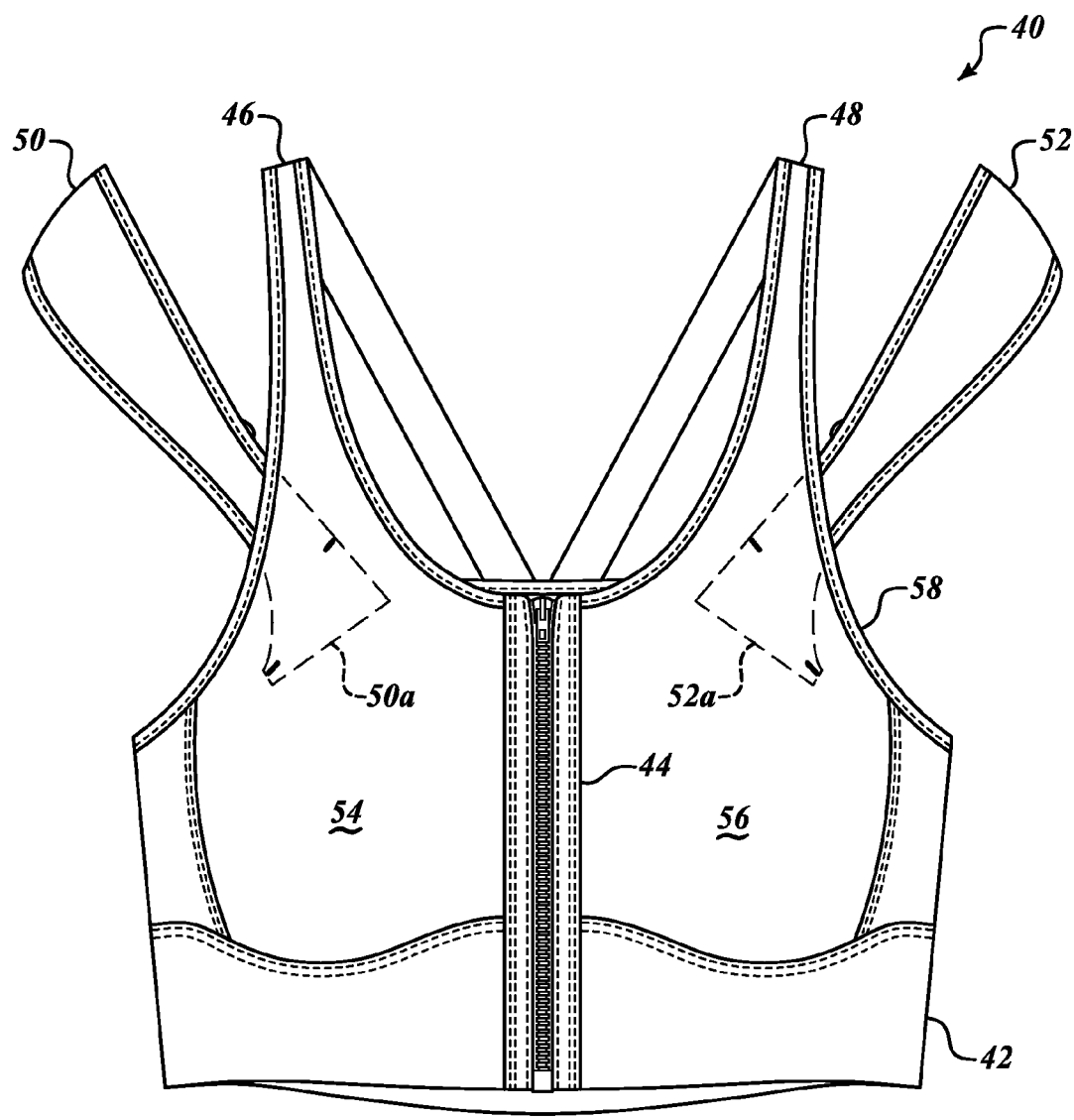
FIG. 2 is a front view of the brassiere embodiment.

The shoulder straps 14 and 16 are permanently attached at their first ends to the front portion of the body band 12 at locations 14a and 16a spaced apart from each other; they attach at the back of the body band 12 at locations 14*b* and 16*b* still spaced apart from each other but in a more central location (i.e., closer to each other and between the wearer's shoulder blades towards the wearer's spine). In alternate embodiments, such as the one shown in the two following figures, the two inner straps may actually cross each other before attaching to the body band. The inner shoulder straps 14 and 16 have the usual intention of holding the posture support garment in place and straightening the wearer's back. This embodiment, similarly to conventional bras, may include means for adjusting the various bra straps in order to fit various sizes and shapes of wearers and also to allow the wearer to adjust them throughout the day. In FIG. 2, this embodiment is shown with conventional buckles 14*c* and 16*c*. Other means for adjusting the straps will be described in more detail later in this specification.

The outer shoulder cap straps 18 and 20 are permanently attached at their first and second ends to the body band 12 in similar fashion at locations on the front portion and on the back portion. They also may be made adjustable with conventional buckles or with other means to be described later. The outer shoulder cap straps 18 and 20 are intended to gird the wearer's shoulders and have the intention of pulling back the wearer's shoulders in order to correct and support the wearer's posture. To this end, the underside of the outer shoulder cap straps may be lined with a gripping material such as silicone both to grip the wearer's skin and pull back and to keep the straps in place.

FIG. 2 shows a preferred embodiment of the invention incorporated into a posture-enhancing brassiere 40 comprising body band 42 (designed to encircle the torso of the wearer—as in a conventional bra) with closure 44, inner shoulder straps 46 and 48, and outer shoulder cap straps 50 and 52. In this embodiment, it is seen that the closure 44 is in the form of a zipper on the front portion of the brassiere, but it could be any other appropriate type of closure, such as a series of hooks-and-eyes or a length of Velcro™, and it also could be located on the side or back portion of the brassiere or body band.

On the front portion of the brassiere, the inner shoulder straps 46 and 48 do not attach to the body band itself, but instead attach at their first ends to the breast cups 54 and 56 (which themselves are attached to the front portion of the body band). The outer shoulder cap straps 50 and 52 also attach at their first ends to the breast cups in the front of the brassiere. In order for the outer cap straps to perform their function of pulling back the shoulders from the area of the pectoral muscles (and not just the skin on the shoulders), it is necessary that they attach at points close to the pectoral muscles, such as at attachment points 50*a* and 52*a*. Depending on the design of the brassiere, these attachment points may coincide with the edge 58, but in this particular embodiment, the edge 58 is located for the wearer's comfort, so the attachment points 50*a* and 52*a* are located further in.

Figure 3A:
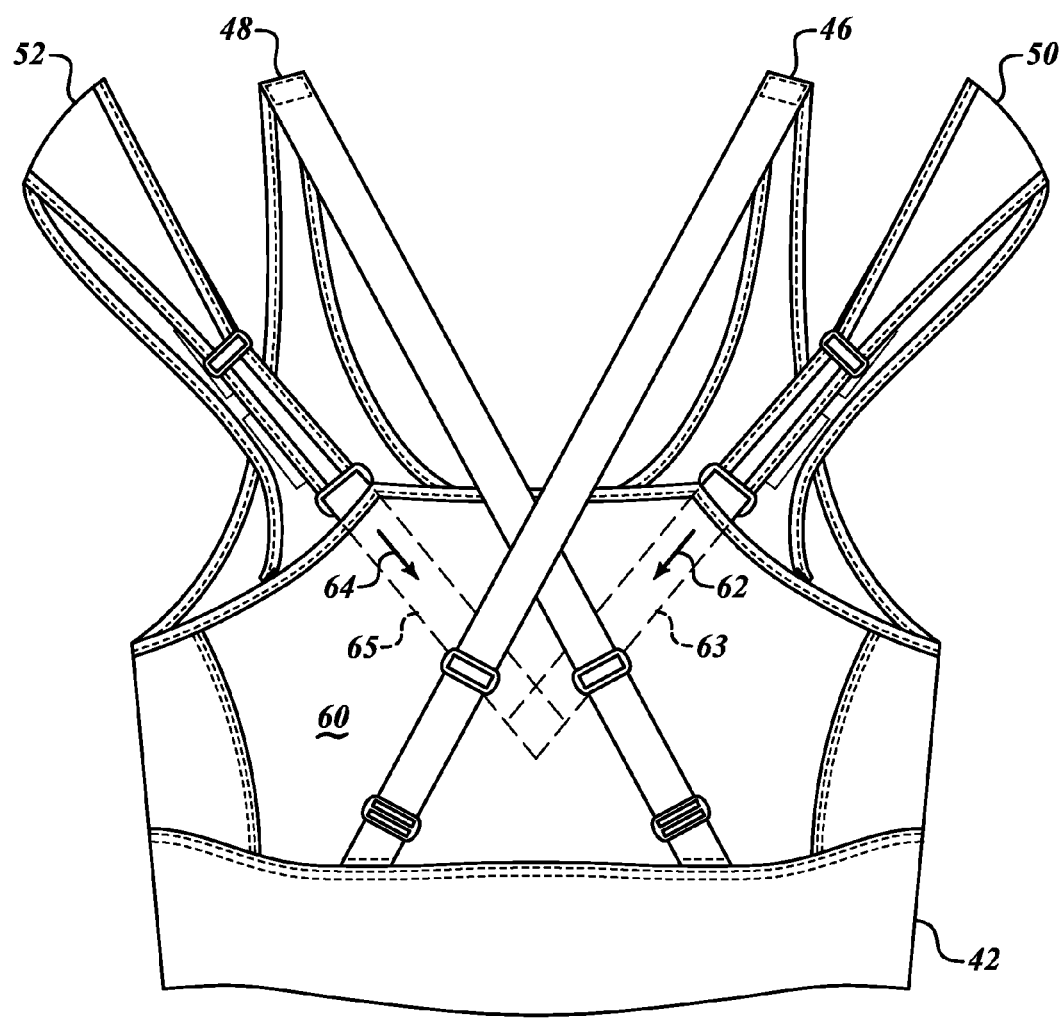
FIG. 3A is a back view of the brassiere embodiment.
Figure 4:
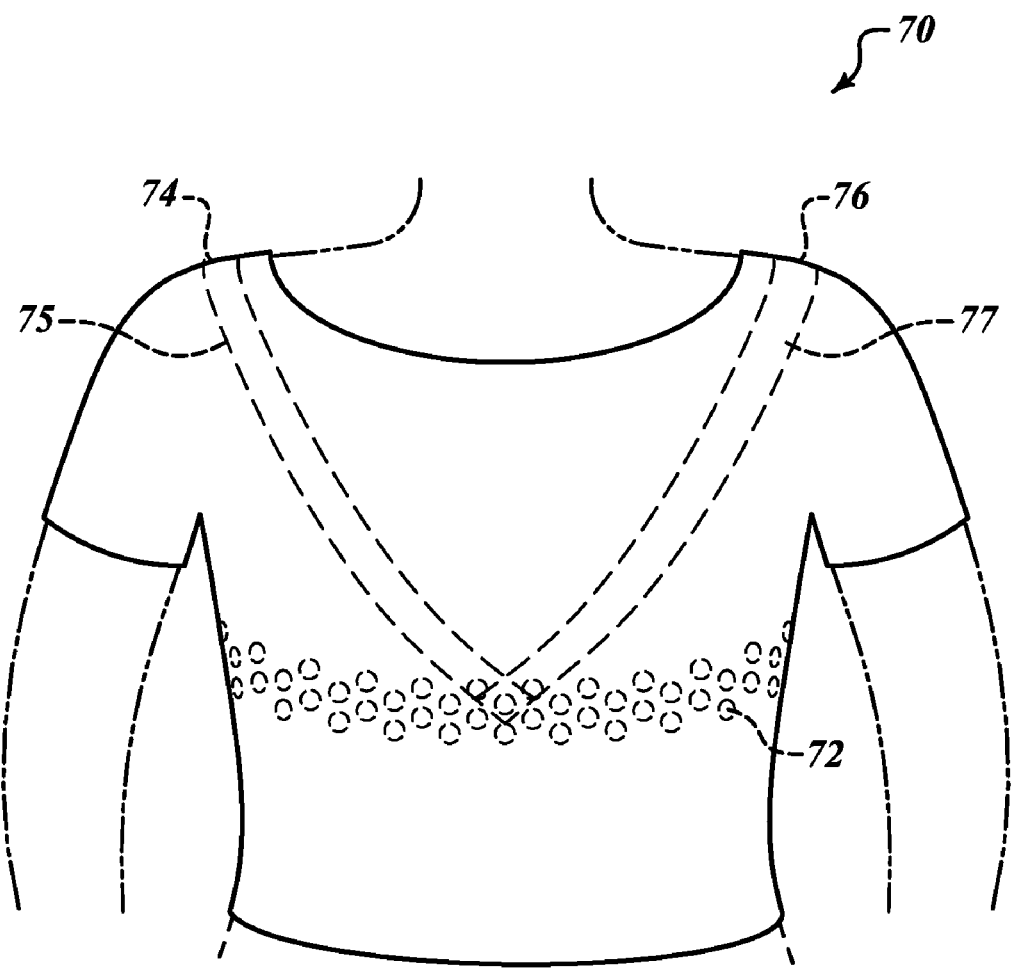
FIG. 4 is a perspective view of an alternate upper garment embodiment.

In the back view of FIG. 3A, it is seen that the inner shoulder straps 46 and 48 cross in the back before attaching at their second ends to the body band 42 and are adjustable with conventional buckles. They could alternatively use a different mechanical or even an electronic means for adjusting, such as discussed below. The outer shoulder cap straps 50 and 52 attach at their second ends to the back panel 60 (which is designed for the wearer's comfort and which is itself attached to the body band) but alternately could attach directly to the body band itself. It is to be noted that the lines of the outer cap straps if extended as shown by the arrows 62 and 64 would form a "V" with its apex generally located at the wearer's spine. Indeed, it is contemplated that in a preferred embodiment, the "V" will be defined and embedded within the back panel as shown by the dashed lines of FIG. 3A. Embedding straps in this way typically locates a strip of flexible material 63 and 65 adjacent the main garment (here the back panel) fabric using sew-free technology or some other adherence method. In this embodiment, the strips 63 and 65 have been layered between the fabric of the back panel 60 and a comfort lining (not shown); however, they could in alternate embodiments be located on either the inside or the outside of the fabric. This strip may have different mechanical properties than the main garment fabric and will function as an embedded strap providing the usual support of a non-embedded, conventional, traditional strap. This construction is also shown in FIG. 4 and may be used to replace the some or all of the invention's elements—i.e., body band, shoulder straps, outer cap straps, shoulder cups, etc. In FIG. 3A, the "V" of the back panel, because the embedded straps are generally aligned with the outer shoulder cap straps, gives the garment and the back stability by resisting twisting and also reinforces the wearer's posture. It is to be noted that the "V" could have its apex closer to the body band (but still close to the wearer's spine) without departing from the invention.

Figure 3B:
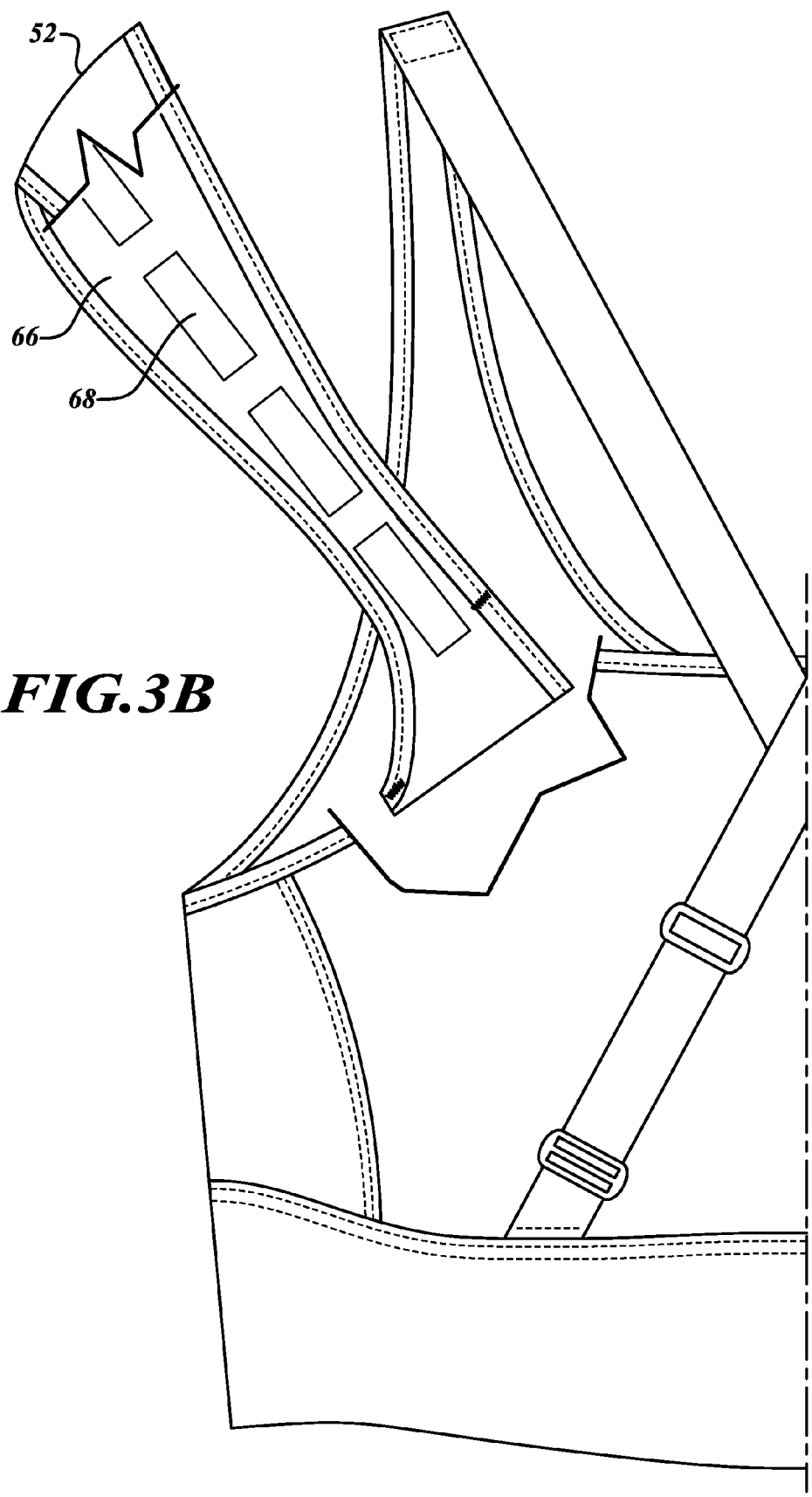
FIG. 3B is a detail view of the underside of an outer cap strap.

FIG. 3B shows one outer shoulder cap strap 52, but it is understood that the opposite cap strap 50 is a mirror image thereof. FIG. 3B shows how in this embodiment, the underside 66 of the outer cap strap is lined with silicone to grip the wearer's skin. The silicone, or other appropriate material, may be applied in patches 68 as shown, or may be dotted or applied in several continuous lines or in any other appropriate configuration. FIG. 3B further shows how the outer shoulder cap strap 52 flares in the area of the top of the shoulder (apex of the strap) in order to "cup" the shoulder. This shoulder cup could alternatively be provided as a separate element, as shown later in FIG. 8.

FIG. 4 shows a possible embodiment of the invention manufactured integrally with an upper posture-support garment, here a top outer garment 70. The body band is shown at 72 and may be constructed by applying a gripping material in dots around the inside of the garment. Alternatively or in addition, the body band 72 could be constructed using the embedded strap technology discussed above and explained further herein following. The embedded flexible strap may be made from a material having a first set of mechanical properties and will have first and second sides. The garment material (base fabric) may have a second set of mechanical properties and will have first and second sides (the first side being defined as the inside of the garment). The first side of the strap may be adhered to the inside of the garment (first side of the base material) using sew-free technology. In this way, the embedded straps will provide the function and support of a non-embedded, traditional, conventional strap. The garment material itself may form the two inner shoulder straps, and the two shoulder cap straps may be constructed by applying a gripping material over the shoulder areas at 74 and 76. Alternatively, the straps could be embedded into the garment 70 such as at 75 and 77. The strap strips could be adhered to the inside of the garment fabric or they could be embedded between two layers of fabric (for instance to provide a layer of comfort next to the wearer's skin).

Figure 5A:
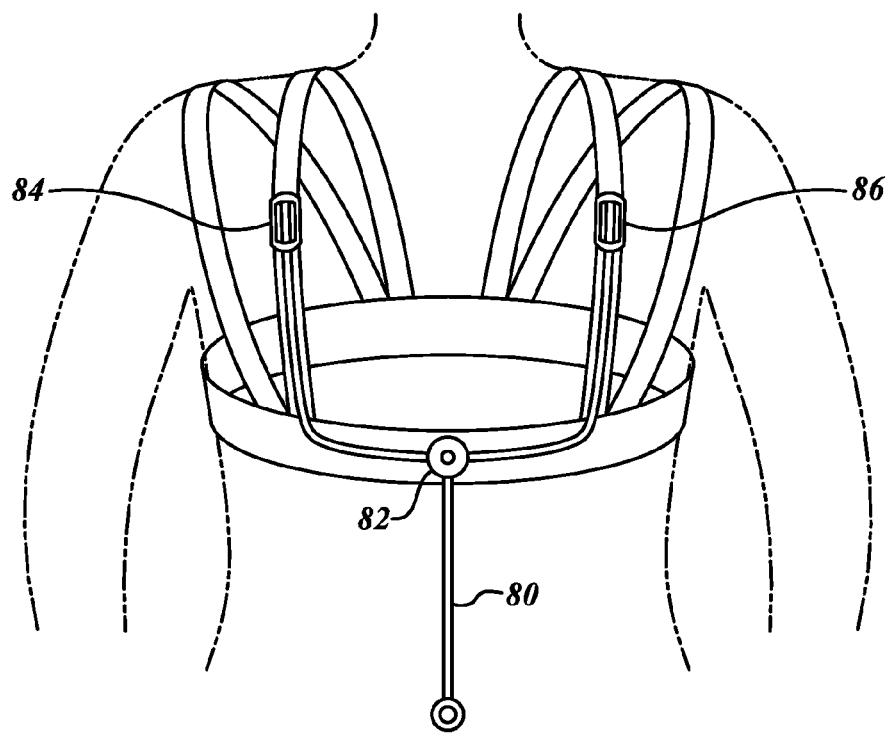
FIG. 5A is a perspective view of a manual adjustment embodiment.
Figure 5B:
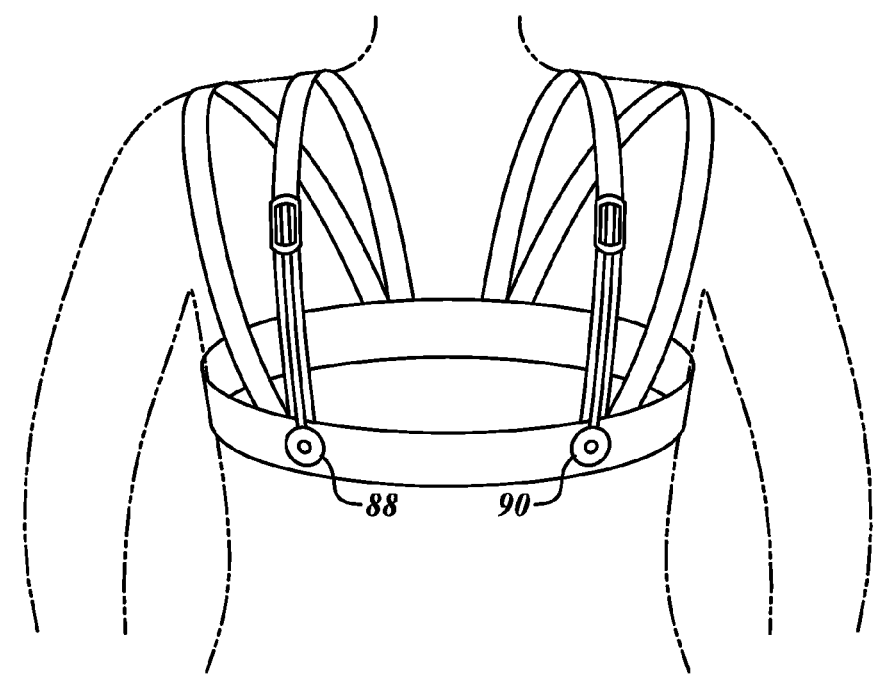
FIG. 5B is a perspective view of an alternate manual adjustment embodiment.

FIGS. 5A and 5B show alternate means for manually adjusting the various straps instead of using conventional buckles. The means for adjusting described in this and successive paragraphs may be used with the instant invention, but also can be applied to any posture support garment having a body band and shoulder straps. In this embodiment shown, a pull cord (or two or more pull cords) may be used. In FIG. 5A, the pull cord 80 is wrapped around a pulley or manual cord retractor 82 located in a convenient location on the body band. The pull cord thence leads to the desired straps. Here, it is shown leading to the two inner shoulder straps at attachment points 84 and 86, but in alternate embodiments, the pull cord could lead to the two outer cap straps. It could even be routed around to the back portion of the body band in order to adjust the straps from that perspective. Alternately, each strap could be fitted with its own pull cord, possibly eliminating the need for a pulley. The cords could then be routed from their respective attachment points on the straps to be easily accessible to the wearer for individual adjustment. FIG. 5B shows such individual strap adjustments; however, in this illustration, the retractors 88 and 90 are controlled with a manual button or crank on the retractor, and there are no cords hanging down.

Figure 6A:
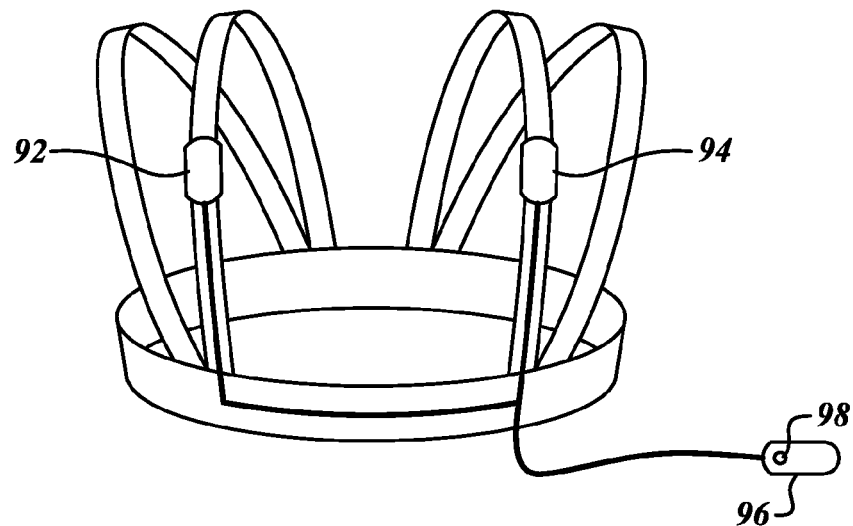
FIG. 6A is a perspective view of an electronic adjustment embodiment.
Figure 6B:
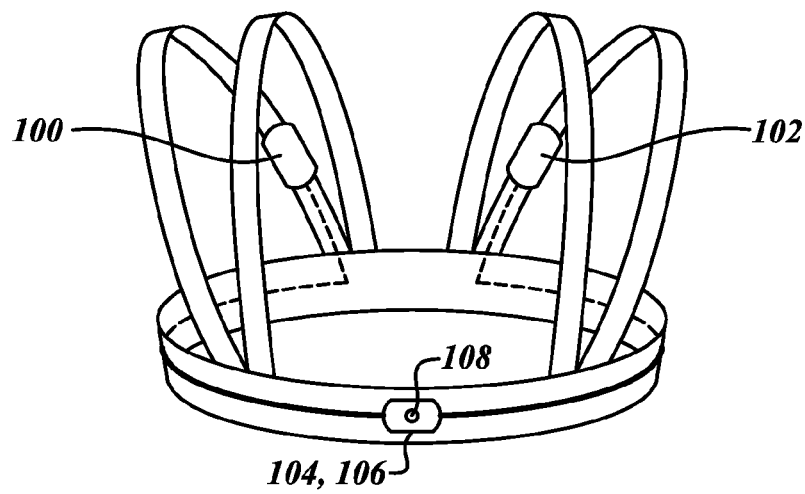
FIG. 6B is a perspective view of an alternate electronic adjustment embodiment.

FIGS. 6A and 6B illustrate electronic means for adjusting the straps, which may be done using electronic textiles, electronic control devices, and /or wireless technology. The length of the straps may be increased or decreased in various electronic ways. For instance, the wearer can adjust the length of the straps by triggering an electronic or electrical mechanism. This automatic tightening/loosening device may be, e.g., a motor that mechanically retracts and releases the straps or an electronic textile (for example, a smart material such as a phase change material, shape memory alloy wire, nitinol, or other electronically reactive materials) whose shape or length changes under electric control. In FIG. 6A, the inner shoulder straps (but it could just as easily be the outer shoulder cap straps) are fitted with electronic strap adjusters 92 and 94 that are wired to the electronic controller 96. In this embodiment, the controller is not fixed to the body band or to the garment but can be a handheld remote or fixed in a watch, wristband, etc. The controller 96 may comprise a button 98 so that the wearer can adjust the straps with a simple touch—for instance a short tap may shorten the straps and a longer press on the button will release them to lengthen. FIG. 6B shows an alternate embodiment wherein the electronic strap adjusters 100 and 102 are applied to the outer cap straps and the wired controller 104 is fixed to the body band at 106. The wearer can tap the button 108 to control the adjustment of the straps. Other combinations of electronic strap adjusters, controllers, and wires may be provided in additional alternate embodiments. There may be separate electronic control devices for separate straps to provide individual adjustment, or one controller may control a pair of straps for balance.

Figure 7A:
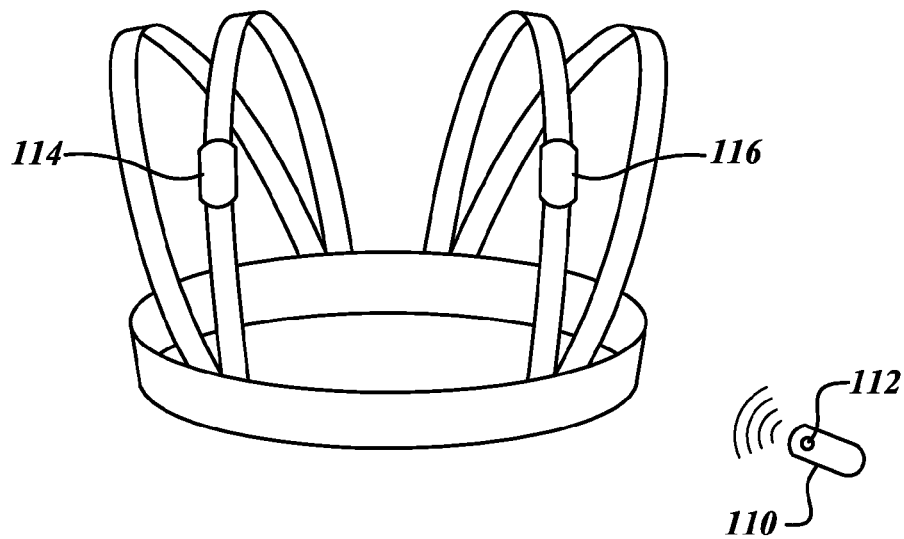
FIG. 7A is a perspective view of an alternate electronic adjustment embodiment.
Figure 7B:
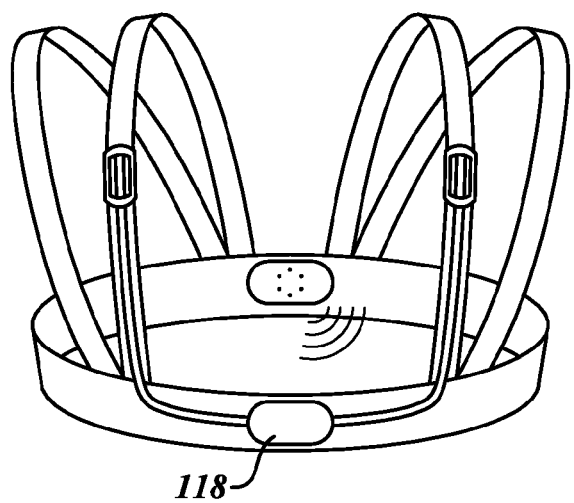
FIG. 7B is a perspective view of another alternate electronic adjustment embodiment.

FIGS. 7A and 7B show examples of how wireless technology can be used to offer more flexibility and discretion to the wearer. Here in FIG. 7A, the controller 110 with button 112 is fitted with wireless technology to communicate directly with the strap adjusters 114 and 116. In FIG. 7B, the strap adjuster 118 is located on the body band itself, is linked (either mechanically or electronically) to the straps at the adjustment points, and responds to a communication signal via Bluetooth™, IPOD™, music player, radio, cell phone, or some other wireless device. Again, there are various combinations or strap adjusters, wireless controllers, and communication devices that can be used within the invention.

Figure 8:
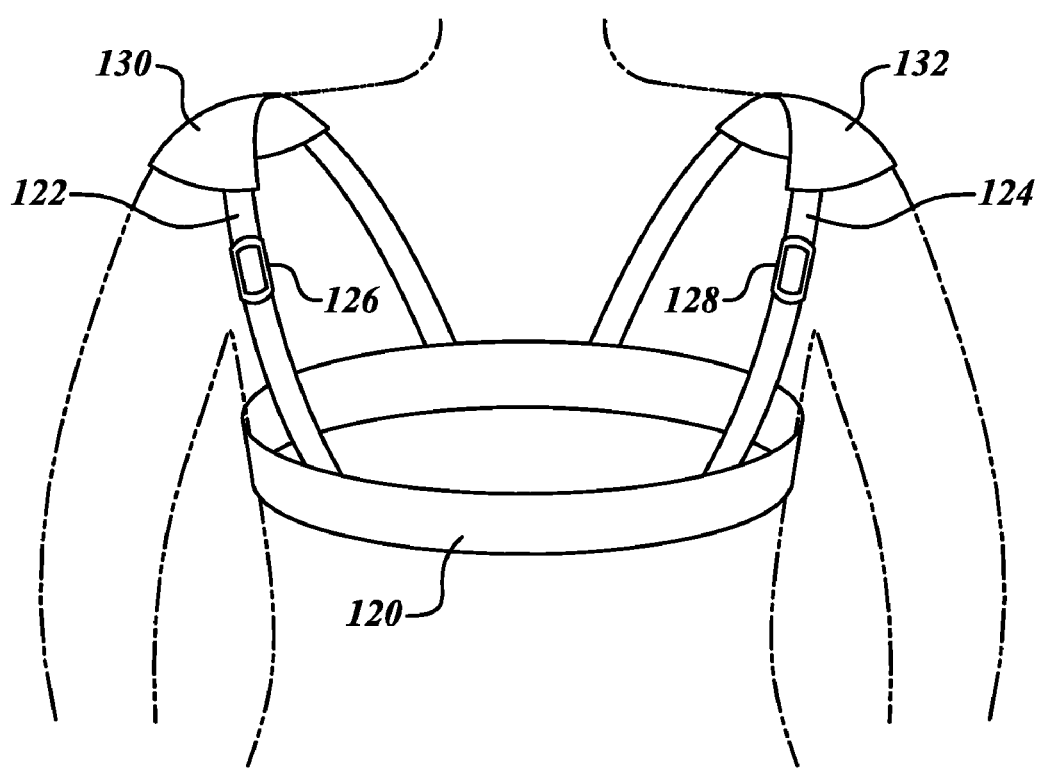
FIG. 8 is a perspective view of an alternate 2-strap design with shoulder cups.

FIG. 8 illustrates a basic posture-enhancing support garment having a body band 120 with front and back portions and two shoulder cap straps 122 and 124. The shoulder cap straps will usually be adjustable—perhaps with conventional buckles 126 and 128 or using one of the mechanical or electronic methods above; their first ends will link to the front portion of the body band (or may attach directly thereto) and their second ends will link to the back portion of the body band (or may attach directly thereto). In addition, the shoulder cap straps may also comprise shoulder cups 130 and 132 linked thereto which may be made of the same material as the straps or a different, more appropriate, material. Moreover, the shoulder cap straps and/or the shoulder cups may be lined with a gripping material as in other embodiments.

In various embodiments mentioned above, the invention uses powered systems with electronic and/or automatic mechanical elements. Power can be supplied in any conventional way, such as with the use of conventional batteries that may be of the button-cell configuration and may also be rechargeable. With manual elements, obviously, no additional power is necessary.

What is claimed is:

1. A posture-enhancing brassiere comprising:
a body band designed to encircle the torso of a wearer, said body band having a front portion and a back portion;
two breast cups attached to said front portion of said body band;
two inner shoulder straps attached to said breast cups at first ends, crossing each other and attaching to said back portion of said body band at second ends;
a pair of outer shoulder cap straps attached to said breast cups at first ends, extending over the shoulder caps of the wearer, and attaching to said body band at second ends, and
wherein said inner shoulder straps are closer to the neck of the wearer than said outer shoulder cap straps.

2. The posture-enhancing brassiere of claim 1 further comprising means for adjusting at least one of said shoulder straps.

3. The posture-enhancing brassiere of claim 1 wherein said shoulder cap straps are lined with a gripping material.

4. The posture-enhancing brassiere of claim 1 further comprising shoulder cups linked to said shoulder cap straps.

5. The posture-enhancing brassiere of claim 2 wherein said means for adjusting comprises elements chosen from the group comprising conventional buckles, other mechanical elements, and electronic elements, wherein said electronic elements comprise electronic strap adjusters attached to at least one of said straps and linked to and controlled by an electronic controller.

6. The posture-enhancing brassiere of claim 5 further comprising a back panel attached to said back portion of said body band, wherein said outer shoulder cap straps attach to said back panel.

7. The posture-enhancing brassiere of claim 6 wherein said back panel includes embedded straps generally aligned with said outer shoulder cap straps, said embedded strap each comprising a strip of flexible material layered between said back panel and a comfort lining.

8. A posture-enhancing support garment comprising:
a body band to encircle the torso of the wearer, said body band defining a front portion and a back portion;
a pair of shoulder cap straps having first and second ends and being attached to said body band such that said first ends link to said front portion of said body band and said second ends link to said back portion of said body band; and
two shoulder CUPS attached to said shoulder cap straps.

9. The posture-enhancing brassiere of claim 1 wherein each of said outer shoulder cap straps is attached to one of said breast cups at two discrete attachment points to be located close to the wearer's pectoral muscles.

10. The posture-enhancing support garment of claim 8 wherein at least one of said shoulder cap straps is adjustable.

11. The posture-enhancing support garment of claim 8 wherein said shoulder cap straps are lined with a grabbing material.

12. The posture-enhancing support garment of claim 11 wherein said body band, said inner shoulder straps, and said shoulder cap straps are made integral with an outer garment.

13. A posture support garment comprising:
   a body band to encircle the wearer's torso; and
   four shoulder straps attached thereto, at least two of said shoulder straps crossing each other, wherein said shoulder straps comprise means for adjusting; and
   at least two shoulder cups attached to at least two of said shoulder straps.

14. The posture support garment of claim 13 wherein said means for adjusting comprises conventional buckles.

15. The posture support garment of claim 13 wherein said means for adjusting comprises at least one pull cord, said pull cord being wrapped around a retractor element located on said body band and leading thence to the desired straps.

16. The posture support garment of claim 13 wherein said means for adjusting comprises a plurality of electronic strap adjusters attached to at least one of said straps and linked to and controlled by an electronic controller linked thereto.

17. The posture support garment of claim 16 wherein said electronic means for adjusting comprises elements chosen from the group comprising electronic textiles, electronic control devices, and wireless technology.

\* \* \* \* \*